United States Patent [19]

Soula

[11] 4,343,745

[45] Aug. 10, 1982

[54] PROCESS FOR SOLUBILIZING ORGANIC OR MINERAL SALTS IN ORGANIC SOLVENTS

[75] Inventor: Gerard Soula, Meyzieu, France

[73] Assignee: Rhone-Poulenc Industries, Paris, France

[21] Appl. No.: 125,775

[22] Filed: Feb. 29, 1980

[30] Foreign Application Priority Data

Mar. 2, 1979 [FR] France ................. 79 05438

[51] Int. Cl.$^3$ ................. C07F 5/06; C07C 85/16; C07C 87/20
[52] U.S. Cl. .................. 260/429 J; 260/439 R; 260/448 R; 260/429.7; 260/429.5; 260/429.3; 260/438.5 R; 260/429.1; 260/429.2; 260/430; 260/446; 260/447; 260/431; 260/438.1; 260/435 R; 260/435 A; 260/429 R; 564/505; 564/508; 564/454; 564/347
[58] Field of Search ............ 260/429 J, 439 R, 448 R, 260/429.7

[56] References Cited

U.S. PATENT DOCUMENTS

| | | | |
|---|---|---|---|
| Re. 28,456 | 7/1975 | Langer et al. | 260/429 J X |
| 3,293,176 | 12/1966 | White | 260/429 J UX |
| 3,734,963 | 5/1973 | Langer et al. | 260/429 J X |
| 3,755,533 | 8/1973 | Langer et al. | 564/508 X |
| 3,758,580 | 9/1973 | Langer et al. | 260/429 J X |
| 3,758,585 | 9/1973 | Bunting | 260/429 J X |
| 3,933,879 | 1/1976 | Langer et al. | 260/429 J X |
| 4,152,401 | 5/1979 | Langer et al. | 260/429 J X |
| 4,179,393 | 12/1979 | Andree et al. | 564/505 X |
| 4,235,811 | 11/1980 | Schulze | 564/505 X |

*Primary Examiner*—Paul F. Shaver
*Attorney, Agent, or Firm*—Burns, Doane, Swecker & Mathis

[57] ABSTRACT

The invention provides a process for solubilizing an organic or mineral salt in an organic solvent, said process comprising contacting an organic or mineral salt of the formula $A^-M^+$, wherein $A^-$ represents a mineral or organic anion and $M^+$ represents a cation selected from the group consisting of the cation $NH_4^+$ and its derivatives and the cations derived from the metals of the groups $I_A$, $II_A$, $III_A$, $IV_A$, $V_A$, $VI_A$, $VII_A$, VIII, $I_B$, $II_B$, $III_B$, $IV_B$ and $V_B$ of the periodic table, with at least one sequestering agent which is soluble in said organic solvent, said sequestering agent having the formula:

$$N[CHR_1-CHR_2-O-(CHR_3-CHR_4-O)_n-R_5]_3 \quad (I)$$

wherein n is an integer from 0 to 10 inclusive; $R_1$, $R_2$, $R_3$ and $R_4$, which can be the same or different, are each a hydrogen atom or an alkyl radical having 1 to 4 carbon atoms; $R_5$ is an alkyl radical having 1 to 12 carbon atoms, a cycloalkyl radical having 3 to 12 carbon atoms, a phenyl radical, a radical of the formula

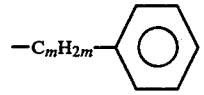

or a radical of the formula

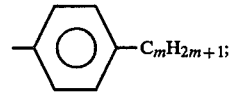

and m is an integer from 1 to 12 inclusive.

The process makes it possible to utilize the $A^-M^+$ salt as a reactant in solvents in which such reaction has not heretofore been possible, or to extract the $A^{31} M^+$ salt from a solution containing it.

49 Claims, No Drawings

PROCESS FOR SOLUBILIZING ORGANIC OR MINERAL SALTS IN ORGANIC SOLVENTS

BACKGROUND OF THE INVENTION

1. Field of the Invention

The present invention provides a process for solubilizing an organic or mineral salt. More particularly, the invention provides a process for solubilizing an organic or mineral salt in an organic solvent in which the organic or mineral salt is not soluble, or for increasing the solubility of an organic or mineral salt in an organic solvent.

2. Background of the Prior Art

The problem of solubilizing salts is a significant one. It is well known that many organic and mineral salts are either insoluble or lack satisfactory solubility in the majority of organic solvents used industrially.

Organic solvents may be classified according to their ability to dissolve a salt. This classification takes into account various factors, such as, specifically, the polar and protonic character of these solvents. It is well known to those skilled in the art that polar solvents, i.e. solvents having a high dielectric constant, dissolve salts more readily than solvents of an apolar character, i.e. those having a low dielectric constant. It is also well known that the best polar solvents are the protonic polar solvents, i.e. solvents having a high dielectric constant and possessing hydrogen atoms of an acid character.

Thus, the best organic solvents to dissolve salts include formamide, acetamide, formic acid, hexamethylphosphorotriamide (H.M.P.T.), dimethylsulfoxide, sulfolane, N-methylpyrrolidone, dimethylformamide, dimethylacetamide, methanol and acetone, while the less good ones include chloroform, methylene chloride, carbon tetrachloride, trichloroethylene, dichloroethane, chlorobenzene, orthodichlorobenzene, benzene, toluene, the xylenes, cyclohexane and hexane.

It should be noted that the difficulty of industrial application of these solvents increases generally when proceeding from the solvents of lesser capability to the better ones. In fact, the better solvents may react with the salts to be dissolved and yield secondary products. Some of them are highly toxic, such as HMPT, while others, such as dimethylsulfoxide, are malodorous and lack thermal stability. Furthermore, all of these products are expensive. It is obvious that persons skilled in the art prefer, when possible, to use an apolar solvent such as toluene and the xylenes, for example, which are less onerous and more easily handled, because of their low toxicity and their thermal and chemical stability.

However, it is very frequently the case that a given salt may be practically totally insoluble in any of the apolar solvents and only partially soluble in the protonic polar solvents, with the maximum solubility being attained in the best of the protonic polar solvents.

It is readily seen therefore, how important it would be to be able to solubilize a salt in a solvent in which it is initially insoluble, but which solvent is easier to apply industrially, or to increase the solubility of the salt in such a solvent. This dual objective is in fact attained by the present invention, with important industrial applications being set forth hereinafter.

From the prior art, a certain amount of work leading to partial solutions in this field is known. Thus, French Patent Application No. 69.43879, published under No. 2,026,481, describes macrocyclic polyether compounds. These compounds can form complexes with the cations of certain metallic compounds, in particular with the salts of alkali metals and alkaline earth metals. These complexes are analytical reagents for use in nonhydroxylated media in which uncomplexed metal compounds are normally insoluble. The macrocyclic compounds described in said French patent application have 15 to 30 atoms in the polyether ring and are composed of 5 to 10 —O-X units, wherein X, for a particular compound, is either (a) —CHR$_1$-CHR$_2$- or (b) —CHR$_1$- CR$_3$R$_4$-CHR$_2$- wherein R$_1$, R$_2$, R$_3$ and R$_4$ are each a hydrogen atom or an alkyl radical.

It is evident that these compounds, which are most commonly called "crown ethers", have a highly sophisticated structure. It follows that the process for their preparation is a delicate operation. Without doubt, one of the major disadvantages of the use of these crown ethers is their extremely high cost, which is a reflection of their complexity and manner of preparation. Another important disadvantage is that, on a practical level, according to the patent application cited above, these compounds can only be used with alkali metal compounds and with compounds of the alkaline earth metals having atomic weights greater than 40.

Another French patent application, Patent Application No. 70.21079, published under No. 2,052,947, also describes macrobicyclic compounds capable of complexing salts and thus rendering them soluble in solvents in which they are normally insoluble. These macrobicyclic compounds, commonly called "cryptants", also have an extremely sophisticated structure, which again implies the disadvantages emphasized above with respect to the crown ethers.

Thus, a real need exists on an industrial level to have available a simple-to-apply process for solubilizing a mineral or organic salt in an organic solvent in which it is not initially soluble or for augmenting the solubility of a mineral or organic salt in an organic solvent. The work of the present applicant lead to the development of such a process.

BRIEF SUMMARY OF THE INVENTION

The present invention thus has as its object a process for solubilizing an organic or mineral salt in an organic solvent in which the salt is not initially soluble, or for augmenting the solubility of an organic or mineral salt in an organic solvent, said process comprising contacting an organic or mineral salt of the formula A$^-$M$^+$, wherein A$^-$ is an organic or mineral anion and M$^+$ is a cation selected from the group consisting of the NH$_4$$^+$ cation and its derivatives and the cations derived from the metals of groups I$_A$, II$_A$, III$_A$, IV$_A$, V$_A$, VI$_A$, VII$_A$, VIII, I$_B$, II$_B$, III$_B$, IV$_B$ and V$_B$ of the perodic table, with at least one sequestering agent soluble in the organic solvent, said sequestering agent having the formula

N[CHR$_1$-CHR$_2$-O-(CHR$_3$-CHR$_4$-O)$_n$-R$_5$]$_3$ wherein n is an integer from 0 to 10 inclusive; R$_1$, R$_2$, R$_3$ and R$_4$, which can be the same or different, are each a hydrogen atom or an alkyl radical having 1 to 4 carbon atoms; R$_5$ is an alkyl radical having 1 to 12 carbon atoms, a cycloalkyl radical having 3 to 12 carbon atoms, a phenyl radical, a radical of the formula

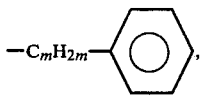

or a radical of the formula

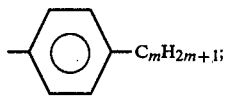

and m is an integer from 1 to 12 inclusive, to afford a complex of said salt and said sequestering agent, said complex having the formula $$[N[CHR_1\text{-}CHR_2\text{-}O\text{-}(CHR_3\text{-}CHR_4\text{-}O)_n\text{-}R_5]_3]_y \quad (M^+A^-) \quad (II)$$

wherein y is greater than or equal to 1 and less than or equal to 3, said complex being soluble in said organic solvent.

DETAILED DESCRIPTION OF THE INVENTION

According to a first variation of the present invention, comprising a single stage, the anhydrous organic or mineral salt and the sequestering agent of formula (I) are contacted in a solution of said organic solvent.

According to a second variation, comprising a single stage, the organic or mineral salt in an aqueous solution is contacted with the sequestering agent of formula (I) in solution in said organic solvent, said organic solvent in this variation being immiscible with water.

According to a third variation of the present process, in a first stage the anhydrous mineral or organic salt in solution in a third solvent is contact with the sequestering agent of formula (I) in solution in the same third solvent; in a second stage, the third solvent is eliminated; and in a third stage, the product resulting from the second stage is contacted with said organic solvent.

According to a fourth variation, in a first stage the anhydrous mineral or organic salt and the sequestering agent of formula (I) are contacted with each other in the absence of any solvent, and in a second stage the product resulting from the first stage is contacted with said organic solvent.

These four variations correspond to different embodiments of the process according to the invention. Those skilled in the art will select from among these four variations according to the nature of the problem to be solved, particularly taking into account the nature of the salt to be solubilized.

The third variation affords ready isolation of the complex of formula (II) obtained at the end of the second stage.

The fourth variation also affords isolation of the complex of formula (II) at the end of the first stage, without it being necessary to employ a third solvent.

The sequestering agents preferred for use in the process of the invention are those wherein $R_1$, $R_2$, $R_3$ and $R_4$ are each a hydrogen atom or a methyl radical, with $R_5$ and n being defined as hereinabove.

Among the preferred sequestering agents, the ones which are particularly preferred are those wherein n is greater than or equal to 0 and less than or equal to 6 and wherein $R_5$ is an alkyl radical having 1 to 4 carbon atoms. Exemplary of the most preferred sequestering agents are the following:

(a) tris(3-oxabutyl)amine of the formula:

(b) tris(3,6-dioxaheptyl)amine of the formula:

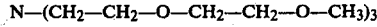

(c) tris(3,6,9-trioxadecyl)amine of the formula:

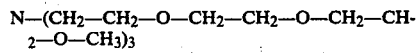

(d) tris(3,6-dioxaoctyl)amine of the formula:

(e) tris(3,6,9-trioxaundecyl)amine of the formula:

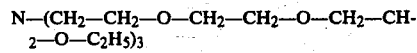

(f) tris(3,6-dioxanonyl)amine of the formula:

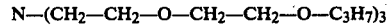

(g) tris(3,6,9-trioxadodecyl)amine of the formula:

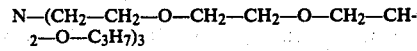

(h) tris(3,6-dioxadecyl)amine of the formula:

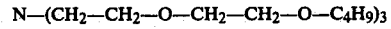

(i) tris(3,6,9-trioxatridecyl)amine of the formula:

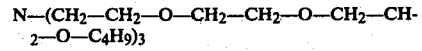

(j) tris(3,6,9,12-tetraoxatridecyl)amine of the formula:

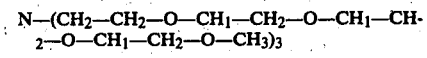

Additional exemplary sequestering agents include:
(h) tris(3,6,9,12,15,18-hexaoxanonadecyl)amine of the formula:

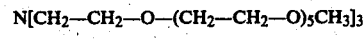

(l) tris(4-methyl-3,6-dioxaheptyl)amine of the formula:

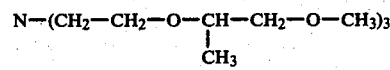

(m) tris(2,4-dimethyl-3,6-dioxaheptyl)amine of the formula:

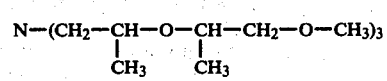

In the definition of the invention given hereinabove, it is obvious that M+ represents both monovalent and polyvalent cations. The same is true for the anion A−, i.e. it represents either monovalent or polyvalent anions.

In spite of the fact that the work of the prior art would lead the researcher to orient his efforts toward complexing molecules of very complicated cyclic structures, the present applicant has discovered that much simpler molecules of a noncyclic structure, and much easier to obtain, yield excellent results.

The amines used in the process of the invention are known as such in the prior art. Thus, French Pat. No. 1,302,365 (corresponding to U.S. Pat. No. 2,928,877) describes a process affording the tertiary amines N—(CH$_2$—CH$_2$—O—CH$_3$)$_3$ and N(CH$_2$—CH$_2$—O—CH$_2$—CH$_2$—O—CH$_3$)$_3$ as byproducts of the synthesis of the corresponding primary and secondary amines, those primary and secondary amines being products of interest as intermediates in the synthesis of pharmaceutical substances, as corrosion inhibitors, as intermediates in the synthesis of agricultural chemicals, and in emulsifiers. The field of application of the compounds obtained in French Pat. No. 1,302,365 thus is quite remote from the use of the compounds of formula (I) in the process of the present invention.

The process of the present invention is particularly suitable for solubilizing A−M+ salts wherein A− is an organic or mineral anion and M+ a cation selected from the group consisting of:

[i] NH$_4$+ and its RNH$_3$+ derivatives wherein R is an alkyl or aryl radical; and

[ii] the cations derived from the metals Li, Na, K, Rb, Cs, Mg, Ca, Sr, Ba, Sc, Y, La and the lanthanides, Ac and the actinides Ti, Zr, Hf, V, Nb, Ta, Cr, Mo, W, Mn, Tc, Re, Fe, Co, Ni, Ru, Rh, Pd, Os, Ir, Pt, Cu, Ag, Au, Zn, Cd, Hg, Al, Ga, In, Tl, Ge, Sn, Pb, Sb, Bi.

However, this preference does not limit the invention in any sense; it derives solely from interest in the process according to the invention on the industrial level.

This same interest also leads to a consideration of the process of the invention as being more particularly, but not exclusively, suitable for solubilizing A−M+ salts wherein A− is selected from the group consisting of:

[i] on the one hand, the mineral anions such as SCN−, O=C=N−, Cl−, Br−, H−, I−, F−, CN−, SH−, S=, OH−, HSO$_3$−, ClO$_4$−, BrO$_4$−, NH$_2$−, NO$_3$−, NO$_2$−, BF$_4$−, BrO−, ClO−, BH$_4$−, SO$_3$−−, PO$_4$−3, CO$_3$−−, SO$_4$−−, ClO$_3$−, BrO$_3$− and AlH$_4$−; and

[ii] on the other hand, the organic anions derived, for example, from:

[a] aliphatic alcohols, such as, for example, methanol (CH$_3$O−) and its higher homologs, cyclopentanol (C$_5$H$_9$O−), cyclohexanol (C$_6$H$_{11}$O−), and benzyl alcohol

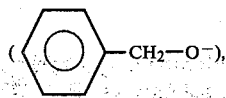

and its higher homologs;

[b] 0 phenols, such as, for example, phenol

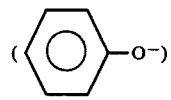

and its derivatives, such as picric acid

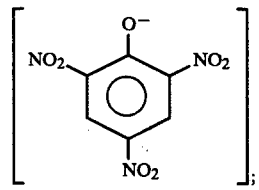

naphthols, such as α-naphthol

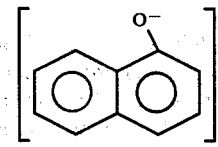

and β-naphthol

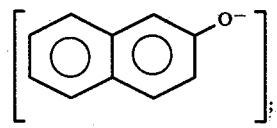

substituted phenols, for example

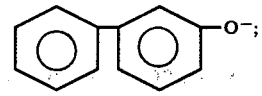

diphenols, for example

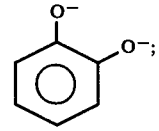

and bisphenols, for example

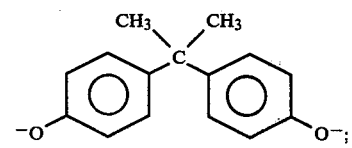

[c] thiols, such as, for example, methylmercaptan (CH$_3$S−) and its higher homologs, and benzylmercaptan

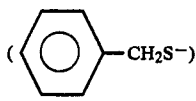

and its homologs;
[d] thiophenols, such as, for example, thiophenol

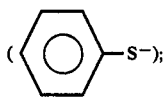

and alkylthiophenols, for example,

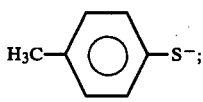

[e] carboxylic acids, such as, for example, acetic acid ($CH_3COO^-$), its higher homologs and its derivatives, such as, for example, cyanoacetic acid ($CNCH_2COO^-$) and chloroacetic acid ($ClCH_2COO^-$); versatic acids, i.e. saturated tertiary monocarboxylic $C_9$–$C_{11}$ acids, for example,

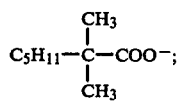

phenylacetic acids

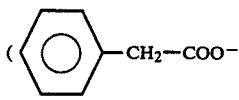

and its homologs); phenoxypropionic acids, for example,

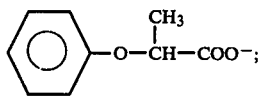

benzoic acids, for example,

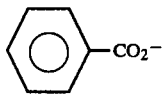

and

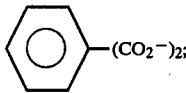

and naphthenic acids

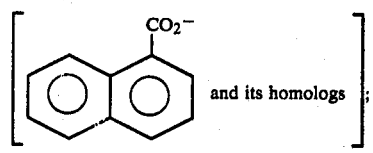

[f] sulfonic acids, such as, for example, methanesulfonic acid ($CH_3$—$SO_3^-$) and its higher homologs; benzenesulfonic acid

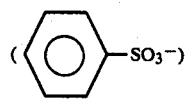

and its homologs; and naphthylsulfonic acid

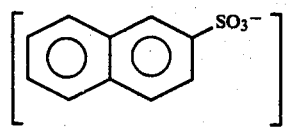

and its homologs;
[g] amines, such as, for example, aliphatic amines, e.g. $CH_3NH^-$ and its higher homologs; anilines, for example,

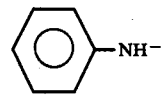

and its homologs;

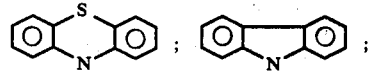

and benzylamines, e.g.

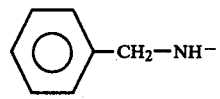

and its homologs;
[h] amides, such as, for example, aliphatic amides ($CH_3CONH^-$ and its higher homologs), and aromatic amides

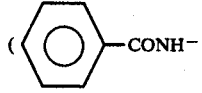

and its homologs);
[i] organic compounds with a mobile hydrogen, such as, for example, the malonic esters [CH—(-$CO_2CH_3$)$_2$, for example]; chloroacetonitrile (Cl—CHCN) and its homologs; phenylacetonitriles, e.g.

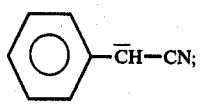

triphenylmethane

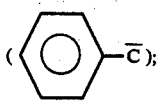

chloroform (CCl₃); alkyl acetylacetonates

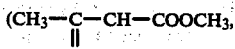

for example); phenylacetone

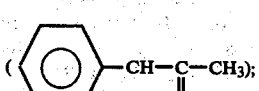

and acetophenones, e.g.

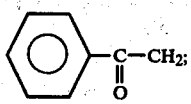

[j] silanols, such as, for example,

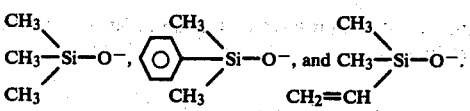

It must be emphasized that the foregoing examples of anions are only illustrative and by no means limiting. In fact, any salt having a cation corresponding to the definition given hereinabove may be treated by the process of the invention.

The selection of the sequestering agent most suitable for solubilizing a given salt must principally take into account the M+ cation; the larger the cation, the greater the number of oxygen atoms contained in the molecule of the sequestering agent should be. For example, potassium picrate in an aqueous solution intimately mixed with methylene chloride does not dissolve in this solvent. If a sequestering agent is added according to the process of the invention, it is observed that the salt is solubilized. The extent of the dissolution will thus be greater with tris(3,6,9-trioxadecyl)amine, which contains three oxygen atoms in each branched chain attached to the nitrogen atom, than with tris(3,6-dioxaheptyl)amine, which contains only two oxygen atoms in each branched chain attached to the nitrogen atom. In contrast, for sodium picrate, because the Na+ cation is smaller than the K+ cation, better solubilization will be obtained with tris(3,6-dioxaheptyl)amine.

The solvent ought to satisfy a certain number of conditions: it must initially dissolve the sequestering agent; and it must also be chemically inert vis-a-vis the salt to be dissolved. (In the same way, it is necessary that the sequestering agent act only as a complexing agent vis-a-vis the mineral or organic salt.)

It must also be emphasized that the more pronounced the apolar nature of the solvent, the more the sequestering agent ought to have a lipophilic character, i.e. the more carbon atoms should be present in the sequestering agent.

In order to obtain the best solubility, the greater the electron density of the A⁻ anion, the more polar the solvent should be. Anions with a high electron density, i.e. the "hard" anions, are anions of small size, such as, for example, OH⁻, F⁻ and Cl⁻. "Soft" anions, which are of a larger size, are, for example, SCN⁻,

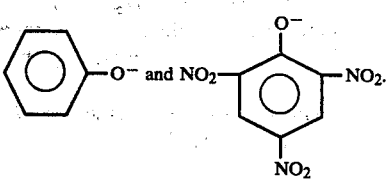

The sequestering agents used in the process according to the invention are soluble in all of the usual organic solvents. More particularly, the process according to the invention solubilizes the salts described above in the following solvents, taken individually or in mixtures: aliphatic solvents such as hexane and cyclohexane; aromatic solvents such as benzene, toluene, o-xylene, m-xylene and p-xylene; halogenated aromatic solvents such as chlorobenzene, o-dichlorobenzene and 1,2,4-trichlorobenzene; halogenated aliphatic solvents such as chloroform, methylene chloride, carbon tetrachloride, 1,2-dichloroethane, 1,1,1-trichloroethane, 1,1,2-trichloroethane, and 1,2,2-trichloro-1,1,2-trifluoroethane; and halogenated olefinic solvents such as perchloroethylene. The invention also affords dissolution in acetone, acetonitrile, dimethylformamide, N-methylpyrrolidone, dimethylacetamide, hexamethylphosphorotriamide, dimethylsulfoxide, sulfolane, methanol, ethanol and isopropanol.

The temperature at which the process is effected can be important. In fact, a salt-sequestering agent complex may be insoluble when cold in the solvent used, but soluble when warm or hot. On the other hand, the temperature used will of course be limited by the boiling point of the solvent employed. Generally speaking, the temperature may vary within broad limits; more particularly, the temperature is generally between about −50° and about 250° C.

The pressure under which the process is carried out is not critical. It is possible to operate at atmospheric pressure, or a pressure above or below atmospheric pressure.

The sequestering agent is generally used in amounts such that the molar ratio of the sequestering agent to the salt to be solubilized is between about 0.001 and about 50. Generally, the greaeter the amount of the sequestering agent, the more complexing will take place and the more extensive the resulting dissolution will be. However, above a ratio of 50, the increase in solubility is no longer significant.

The process according to the invention may be applied to a large number of fields of industrial chemistry.

It will be obvious to those skilled in the art that the dissolution obtained according to the process of the invention makes it possible to react the salt under consideration with a substrate in solvents wherein such a reaction has not heretofore been possible, which will be of great interest in numerous cases of organic synthesis. This is the case of the first variation discussed hereinabove.

Another interesting application concerns the extraction of metals. A metallic compound $A^-M^+$ may be extracted from a solution by making it pass, by means of complex formation according to the invention, from an organic or aqueous phase into another organic phase. This is the case of the second variant discussed hereinabove. For example, it is possible in this manner to extract from an aqueous solution of picrates of alkali and alkaline earth metals, as well as Ag picrate, using a sequestering agent according to the invention in methylene chloride. Alkali metal thiocyanates may be similarly extracted.

The present invention also concerns as novel products, the complexes of the formula:

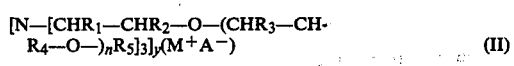     (II)

wherein $R_1$, $R_2$, $R_3$, $R_4$, $R_5$, n, $M^+$, $A^-$ and y are defined generally and preferentially as hereinabove, which are formed in the process of the invention.

Even more partcularly, the invention concerns the following complexes:

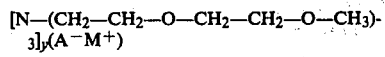

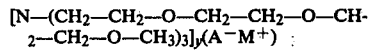

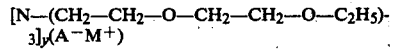

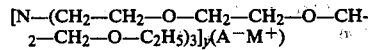

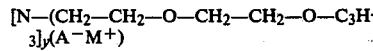

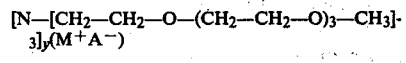

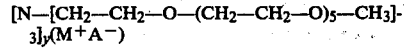

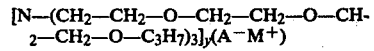

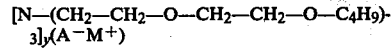

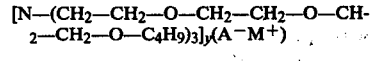

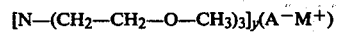

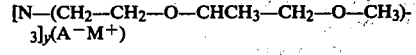

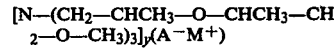

wherein $A^-$, $M^+$ and y are defined as above.

The sequestering agent used in the process according to the invention can be prepared by the condensation of a salt of the formula:

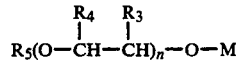

wherein $R_3$, $R_4$, $R_5$ and n have their previously defined meanings, and wherein M represents an alkali metal atom chosen from among sodium, potassium and lithium, either with an amine of the general formula:

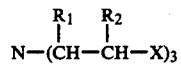

wherein $R_1$ and $R_2$ have the significance indicated hereinabove and X represents chlorine or bromine, or with the corresponding hydrochloride or hydrobromide.

The molar ratio of the alkali metal salt to the amine is between approximately 3 and approximately 5.

The condensation reaction is effected at a temperature of between about 100° and about 150° C., for a period of time of from about 1 to about 15 hours, and in the presence of a suitable solvent, for example, chlorobenzene or, preferably, a monoalkyether of ethylene glycol of the formula $R_5$—$(O$—$CHR_4$—$CHR_3)_n$—OH wherein $R_3$, $R_4$, $R_5$ and n are defined as before.

The reaction is preferably carried out so that a solution containing 2 to 5 moles of the alkali metal salt is present per liter of the solvent.

The mixture at the end of the reaction contains principally a tertiary amine of the formula:

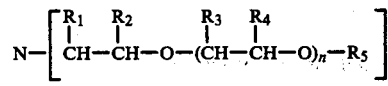

but also contains, in a small amount, a secondary amine of the formula:

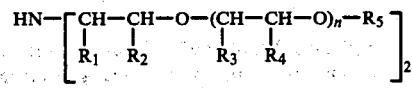

and traces of a primary amine of the formula:

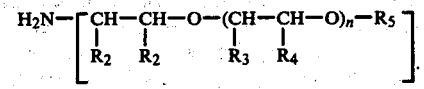

The tertiary, secondary and primary amines are generally obtained in a ratio of approximately 90:8:2, respectively, after distillation.

The mixture obtained after the first distillation, i.e. containing the three types of amines, may be used directly in the process of the invention. However, in a preferred embodiment of the invention, a more stringent distillation of the mixture is effected in order to obtain an essentially pure tertiary amine.

Other characteristics and advantages of the invention will appear from the examples which follow hereafter. These examples are set forth merely for purposes of illustration and are not to be considered as limiting the range of the present invention.

In the examples, the solubilities measured and the calculated maximum solubilities are expressed in terms of the metal content in the solution. The maximum calculated solubility corresponds to the case wherein all of the salt involved passes into solution. The proportion dissolved represents the ratio of the measured solubility to the maximum calculated solubility, i.e. it expresses the proportion of the complexed salt passing into solution. The formulas of complexes given are those of the complexes passing into solution in the solvent under consideration.

EXAMPLE 1

Direct Solubilization of Tungsten Hexachloride in Methylene Chloride

In a 50 ml Erlenmeyer flask equipped with an ascending cooler and a magnetic agitator, 20 ml of anhydrous, purified methylene chloride (i.e. without stabilizer) are introduced. Subsequently, 0.4 g of tungsten hexachloride (0.001 mole) and 0.32 g of tris(3,6-dioxaheptyl)amine (0.001 mole) are added.

The mixture is agitated for 10 minutes at ambient temperature, then is centrifuged. The clear solution obtained in this manner is analyzed by flame spectrometry.

Measured solubility: 9290 mg/l.
Maximum calculated solubility: 9295 mg/l.
Proportion dissolved: 99%.
Complex formed: $[N(CH_2-CH_2-O-CH_2-CH_2-O-CH_3)_3](WCl_6)$.

Comparative experiment. The operation is performed as above, but without the addition of tris(3,6-dioxaheptyl)amine.

Measured solubility: 500 mg/l.

EXAMPLE 2

Direct Solubilization of Iridium Trichloride in Methylene Chloride

The operation is performed according to the procedure of Experiment 1, but using the following reagents:
$IrCl_3 = 0.297$ g (0.001 mole)
tris(3,6-dioxaheptyl)amine = 0.32 g (0.001 mole)
$CH_2Cl_2 = 20$ cm$^3$.
Measured solubility: 9500 mg/l.
Maximum calculated solubility: 9580 mg/l.
Proportion dissolved: 99%.
Complex formed: $[N(CH_2-CH_2-O-CH_2-CH_2-O-CH_3)_3]$ $(IrCl_3)$.

Comparative experiment. The operation is effected as above, but without the addition of tris(3,6-dioxaheptyl)amine.

Measured solubility: less than 1 mg/l.

EXAMPLE 3

Direct Solubilization of Rhenium Trichloride in Methylene Chloride

The operation is performed according to the procedure of Example 1, but using the following reagents:
$ReCl_3 = 0.292$ g (0.001 mole)
Tris(3,6-dioxaheptyl)amine = 0.32 g (0.001 mole)
$CH_2Cl_2 = 20$ cm$^3$.
Measured solubility: 9300 mg/l.
Maximum calculated solubility: 9310 mg/l.
Proportion dissolved: 99%.
Complex formed: $[N(CH_2-CH_2-O-CH_2-CH_2-O-CH_3)_3]$ $(ReCl_3)$.

Comparative experiment. The operation is effected as above, but without the addition of tris(3,6-dioxaheptyl)amine.

Measured solubility: less than 1 mg/l.

EXAMPLE 4

Direct Solubilization of Ruthenium Trichloride in Methylene Chloride

The operation is effected as in Example 1, but using the following reagents:
$RuCl_3 = 0.207$ g (0.001 mole)
Tris(3,6-dioxaheptyl)amine = 0.32 g (0.001 mole)
$CH_2Cl_2 = 20$ cm$^3$.
Measured solubility: 5000 mg/l.
Maximum calculated solubility: 5050 mg/l.
Proportion dissolved: 99%.
Complex formed: $[N(CH_2-CH_2-O-CH_2-CH_2-O-CH_3)_3]$ $(RuCl_3)$.

Comparative experiment. The operation is carried out as above, but without the addition of tris(3,6-dioxaheptyl)amine.

Measured solubility: less than 1 mg/l.

EXAMPLE 5

Direct Solubilization of Molybdenum Pentachloride in Methylene Chloride

The operation is performed as in Example 1, but using the following reagents:
$MoCl_5 = 0.273$ g (0.001 mole)
Tris(3,6-dioxaheptyl)amine = 0.32 g (0.001 mole)
$CH_2Cl_2 = 20$ cm$^3$
Measured solubility: 4250 mg/l.
Maximum calculated solubility: 4800 mg/l.
Proportion dissolved: 88%.
Complex formed: $[N(CH_2-CH_2-O-CH_2-CH_2-O-CH_3)_3]$ $(MoCl_5)$.

Comparative experiment. The operation is effected as above, but without the addition of tris(3,6-dioxaheptyl)amine.

Measured solubility: 1360 mg/l.

EXAMPLE 6

Direct Solubilization of Rhodium Trichloride in Methylene Chloride

The operation is effected as in Example 1, but using the following reagents:
$RhCl_3 = 0.209$ g (0.001 mole)
Tris(3,6-dioxaheptyl)amine = 0.32 g (0.001 mole)
$CH_2Cl_2 = 20$ cm$^3$.
Measured solubility: 5100 mg/l.
Maximum calculated solubility: 5150 mg/l.
Proportion dissolved: 99%.
Complex formed. $[N(CH_2-CH_2-O-CH_2-CH_2-O-CH_3)_3]$ $(RhCl_3)$ Comparative experiment. The operation is effected as above, but without the addition of tris(3,6-dioxaheptyl)amine.

Measured solubility: less than 2 mg/l.

EXAMPLE 7

Direct Solubilization of Palladium Chloride in Methylene Chloride

The operation is performed as in Example 1, but using the following reagents:
$PdCl_2 = 0.177$ g (0.001 mole)
Tris(3,6-dioxaheptyl)amine = 0.32 g (0.001 mole)
$CH_2CH_2 = 20$ cm$^3$.
Measured solubility: 2600 mg/l.
Maximum calculated solubility: 5320 mg/l.

Proportion dissolved: 49%.
Comparative experiment. The operation is effected as above, but without the addition of tris(3,6-dioxaheptyl)amine.
Solubility measured: less than 2 mg/l.

EXAMPLE 8

Direct Solubilization of Platinum Chloride in Methylene Chloride

The operation is performed as in Example 1, but using the following reagents:
$PtCl_2 = 0.266$ g (0.001 mole)
Tris(3,6-dioxaheptyl)amine = 0.32 g (0.001 mole)
$CH_2Cl_2 = 20$ cm$^3$.
Measured solubility: 9700 mg/l.
Maximum calculated solubility: 9755 mg/l.
Proportion dissolved: 99%.
Complex formed: $[N(CH_2-CH_2-O-CH_2-CH_2-O-CH_3)_3]$ $(PtCl_2)$.
Comparative experiment. The operation is effected as above, but without the addition of tris(3,6-dioxaheptyl)amine.
Measured solubility: less than 1 mg/l.

EXAMPLE 9

Direct Solubilization of Tantalum Pentafluoride in Methylene Chloride

The operation is performed as in Example 1, but using the following reagents:
$TaF_5 = 0.276$ g (0.001 mole)
Tris(3,6-dioxaheptyl)amine = 0.32 g (0.001 mole)
$CH_2Cl_2 = 20$ cm$^3$.
Measured solubility: 2420 mg/l.
Maximum calculated solubility: 9050 mg/l.
Proportion dissolved: 26%.
Comparative experiment. The operation is effected as above, but without the addition of tris(3,6-dioxaheptyl)amine.
Solubility measured: less than 1 mg/l.

EXAMPLE 10

Direct Solubilization of Iron Chloride (Ferrous) in Methylene Chloride

The operation is performed as in Example 1, but using the following reagents:
$FeCl_2 \cdot 4\,H_2O = 0.199$ g (0.001 mole)
Tris(3,6-dioxaheptyl)amine = 0.32 g (0.001 mole)
$CH_2Cl_2 = 20$ cm$^3$.
Measured solubility: 950 mg/l.
Maximum calculated solubility: 2794 mg/l.
Proportion dissolved: 34%.
Comparative experiment. The experiment is effected as above, but without the addition of tris(3,6-dioxaheptyl)amine.
Solubility measured: 2 mg/l.

EXAMPLE 11

Direct Solubilization of Molybdenum Hexacarbonyl in Methylene Chloride

The operation is performed as in Example 1, but using the following reagents:
$Mo(CO)_6 = 0.276$ g (0.001 mole)
Tris(3,6-dioxaheptyl)amine = 0.32 g (0.001 mole)
$CH_2Cl_2 = 20$ cm$^3$.
Measured solubility: 4780 mg/l.
Maximum calculated solubility: 4797 mg/l.
Proportion dissolved: 99%.
Comparative experiment. The operation is effected as above, but without the addition of tris(3,6-dioxaheptyl)amine.
Solubility measured: less than 1 mg/l.

EXAMPLE 12

Direct Solubilization of Titanium Chloride in Methylene Chloride

The operation is performed as in Example 1, but using the following reagents:
$TiCl_3 = 0.157$ g (0.001 mole)
Tris(3,6-dioxaheptyl)amine = 0.32 g (0.001 mole)
$CH_2Cl_2 = 20$ cm$^3$.
Measured solubility: 2390 mg/l.
Maximum calculated solubility: 2395 mg/l.
Proportion dissolved: 99%.
Complex formed: $[N(CH_2-CH_2-O-CH_2-CH_2-O-CH_3)_3]$ $(TiCl_3)$.
Comparative experiment. The operation is effected as above, but without the addition of tris(3,6-dioxaheptyl)amine.
Solubility measured: less than 1 mg/l.

EXAMPLE 13

Direct Solubilization of Magnesium Perchlorate in Methylene Chloride

The operation is performed as in Example 1, but using the following reagents:
$Mg(ClO_4)_2 \cdot H_2O = 0.223$ g (0.001 mole)
Tris(3,6-dioxaheptyl)amine = 0.32 g (0.001 mole)
$CH_2Cl_2 = 20$ cm$^3$.
Measured solubility: 14 mg/l.
Maximum calculated solubility: 1215 mg/l.
Proportion dissolved: 1%.
Comparative experiment. The operation is effected as above, but without the addition of tris(3,6-dioxaheptyl)amine.
Measured solubility: less than 0.4 mg/l.

EXAMPLE 14

Direct Solubilization of Selected Zinc Salts in Methylene Chloride

The operation is performed as in Example 1, but using the following reagents:
(a)
$ZnCl_2 = 0.136$ g (0.001 mole)
Tris(3,6-dioxaheptyl)amine = 0.32 g (0.001 mole)
$CH_2Cl_2 = 20$ cm$^3$.
Measured solubility: 2190 mg/l.
Maximum calculated solubility: 3270 mg/l.
Proportion dissolved: 67%.
Comparative experiment. The operation is effected as above, but without the addition of tris(3,6-dioxaheptyl)amine.
Solubility measured: less than 1 mg/l.
(b)
$Zn(NO_3)_2 \cdot 6\,H_2O = 0.297$ g (0.001 mole)
Tris(3,6-dioxaheptyl)amine = 0.32 g (0.001 mole)
$CH_2Cl_2 = 20$ cm$^3$.
Solubility measured: 81 mg/l.
Maximum solubility calculated: 3270 mg/l.
Proportion dissolved: 2%.
Comparative experiment. The operation is effected as above, but without the addition of tris(3,6-dioxaheptyl)amine.

Solubility measured: less than 1 mg/l.

EXAMPLE 15

Direct Solubilization of Selected Nickel Salts in Methylene Chloride

The operation is performed as in Example 1, but using the following reagents:

(a)
$NiCl_2.6\ H_2O = 0.238$ g (0.001 mole)
Tris(3,6-dioxaheptyl)amine = 0.32 g (0.001 mole)
$CH_2Cl_2 = 20$ cm$^3$.
Measured solubility: 800 mg/l.
Maximum calculated solubility: 2935 mg/l.
Proportion dissolved: 27%.

Comparative experiment: The operation is effected as above, but without the addition of tris(3,6-dioxaheptyl)amine.
Solubility measured: less than 1 mg/l.

(b)
$(CH_3COO)_2\ Ni.4\ H_2O = 0.249$ g (0.001 mole)
Tris(3,6-dioxaheptyl)amine = 0.32 g (0.001 mole)
$CH_2Cl_2 = 20$ cm$^3$.
Solubility measured: 250 mg/l.
Maximum calculated solubility: 2935 mg/l.
Proportion dissolved: 8.5%.

Comparative experiment. The operation is effected as above, but without the addition of tris(3,6-dioxaheptyl)amine.
Solubility measured: less than 1 mg/l.

EXAMPLE 16

Direct Solubilization of Selected Cobalt Salts in Methylene Chloride

The operation is performed as in Example 1, but using the following reagents:

(a)
$CoCl_2.6\ H_2O = 0.238$ g (0.001 mole)
Tris(3,6-dioxaheptyl)amine = 0.32 g (0.001 mole)
$CH_2Cl_2 = 20$ cm$^3$.
Solubility measured: 1100 mg/l.
Maximum calculated solubility: 2950 mg/l.
Proportion dissolved: 37%.

Comparative experiment. The operation is effected as above, but without the addition of tris(3,6-dioxaheptyl)amine.
Solubility measured: less than 1 mg/l.

(b)
$CoBr_2.2\ H_2O = 0.255$ g (0.001 mole)
Tris(3,6-dioxaheptyl)amine = 0.32 g (0.001 mole)
$CH_2Cl_2 = 20$ cm$^3$
Solubility measured: 800 mg/l.
Maximum calculated solubility: 2950 mg/l.
Proportion dissolved: 27%.

Comparative experiment. The operation is effected as above, but without the addition of tris(3,6-dioxaheptyl)amine.
Solubility measured: less than 1 mg/l.

(c)
$(CH_3COO)_2\ Co.4\ H_2O = 0.242$ g (0.001 mole)
Tris(3,6-dioxaheptyl)amine = 0.32 g (0.001 mole)
$CH_2Cl_2 = 20$ cm$^3$.
Solubility measured: 150 mg/l.
Maximum calculated solubility: 2950 mg/l.
Proportion dissolved: 5%.

Comparative experiment. The operation is effected as above, but without the addition of tris(3,6-dioxaheptyl)amine.
Solubility measured: 5 mg/l.

EXAMPLE 17

Direct Solubilization of Chromium Acetate in Methylene Chloride

The operation is performed as in Example 1, but using the following reagents:
$(CH_3COO)_3Cr = 0.229$ g (0.001 mole)
Tris(3,6-dioxaheptyl)amine = 0.32 g (0.001 mole)
$CH_2Cl_2 = 20$ cm$^3$.
Solubility measured: 67 mg/l.
Maximum calculated solubility: 2600 mg/l.
Proportion dissolved: 2%.

Comparative experiment. The operation is effected as above, but without tris(3,6-dioxaheptyl)amine.
Solubility measured: less than 1 mg/l.

EXAMPLE 18

Direct Solubilization of Mercury Chloride in Methylene Chloride

Two experiments are performed using the procedure of Example 1, but differing in the nature of the sequestering agent employed.

Experiment 1

$HgCl = 0.236$ g (0.001 mole).
Tris(3,6-dioxaheptyl)amine = 0.32 g (0.001 mole).
$CH_2Cl_2 = 20$ cm$^3$.
Solubility measured: 1200 mg/l.
Maximum calculated solubility: 10020 mg/l.
Proportion dissolved: 12%.

Comparative experiment. The operation is effected as above, but without the addition of tris(3,6-dioxaheptyl)amine.
Solubility measured: 33 mg/l.

Experiment 2

$HgCl = 0.236$ g (0.001 mole).
Tris(3,6,9-trioxadecyl)amine = 0.455 g (0.001 mole).
$CH_2Cl_2 = 20$ cm$^3$.
Solubility measured: 9300 mg/l.
Maximum calculated solubility: 10020 mg/l.
Proportion dissolved: 93%.
Complex formed: $[N(CH_2-CH_2-O-CH_2-CH_2-O-CH_2-CH_2-O-CH_3)_3]\ (HgCl)$.

Comparative experiment. The operation is effected as above, but without the addition of tris(3,6,9-trioxadecyl)amine.
Solubility measured: 30 mg/l.

Thus, it has been found that the solubility of mercury chloride increases with the number of oxygen atoms contained in the molecule of the sequestering agent.

EXAMPLE 19

Direct Solubilization of Mercury Nitrate in Methylene Chloride

Two experiments are performed using the procedure of Example 1, but differing in the nature of the sequestering agent employed.

Experiment 1

$HgNO_3.H_2O = 0.281$ g (0.001 mole).
Tris(3,6-dioxaheptyl)amine = 0.32 g (0.001 mole).
$CH_2Cl_2 = 20$ cm$^3$.
Solubility measured: 600 mg/l.
Maximum calculated solubility: 10020 mg/l.

Proportion dissolved: 6%.

Comparative experiment. The operation is effected as above, but without the addition of tris(3,6-dioxaheptyl)amine.

Solubility measured: 33 mg/l.

Experiment 2

$HgNO_3.H_2O = 0.281$ g (0.001 mole).
Tris(3,6,9-trioxadecyl)amine = 0.455 g (0.001 mole).
$CH_2Cl_2 = 20$ cm$^3$.
Solubility measured: 1200 mg/l.
Maximum calculated solubility: 10020 mg/l.
Proportion dissolved: 12%.

Comparative experiment. The operation is effected as above, but without the addition of tris(3,6,9-trioxadecyl)amine.

Solubility measured: 30 mg/l.

Here again, it has been found that solubility increases with the number of oxygen atoms contained in the molecule of the sequestering agent.

EXAMPLE 20

Direct Solubilization of Calcium Chloride in Methylene Chloride

The operation is performed generally as in Example 1, except that the mixture is agitated for a few minutes and then allowed to decant overnight, using the following reagents:

$CaCl_2 = 0.111$ g (0.001 mole)
Tris(3,6-dioxaheptyl)amine = 0.32 g (0.001 mole)
$CH_2Cl_2 = 10$ cm$^3$.
Solubility measured: 2000 mg/l.
Maximum calculated solubility: 4000 mg/l.
Proportion dissolved: 50%.

Comparative experiment. The operation is effected as above, but without the addition of tris(3,6-dioxaheptyl)amine.

Solubility measured: less than 1 mg/l.

EXAMPLE 21

Direct Solubilization of Copper Thiocyanate in Methylene Chloride

The operation is performed as in Example 1, except that the mixture is agitated for a few minutes and then allowed to decant overnight, using the following reagents:

CuSCN = 0.122 g (0.001 mole)
Tris(3,6-dioxaheptyl)amine = 0.32 g (0.001 mole)
$CH_2Cl_2 = 10$ cm$^3$.
Solubility measured: 140 mg/l.
Maximum calculated solubility: 6355 mg/l.
Proportion dissolved: 2%.

Comparative experiment. The operation is effected as above, but without the addition of tris(3,6-dioxaheptyl)amine.

Solubility measured: less than 1 mg/l.

EXAMPLE 22

Direct Solubilization of Mercury Thiocyanate in Methylene Chloride

The operation is performed as in Example 1, except that the mixture is agitated for a few minutes and then allowed to decant overnight, using the following reagents:

$Hg(SCN)_2 = 0.316$ g (0.001 mole)
Tris(3,6-dioxaheptyl)amine = 0.32 g (0.001 mole)
$CH_2Cl_2 = 10$ cm$^3$.
Solubility measured: 20,000 mg/l.
Maximum calculated solubility: 20060 mg/l.
Proportion dissolved: 99%.
Complex formed: $[N(CH_2-CH_2-O-CH_2-CH_2-O-CH_3)_3]Hg(SCN)_2$.

Comparative experiment. The operation is effected as above, but without the addition of tris(3,6-dioxaheptyl)amine.

Solubility measured: less than 10 mg/l.

EXAMPLE 23

Direct Solubilization of Tungsten Hexachloride in Toluene

Into a 50 ml Erlenmeyer flask, equipped with an ascending cooler and a magnetic agitator, are introduced 20 ml of toluene. Then, 0.4 g of tungsten hexachloride (0.001 mole) and 0.365 g tris(3,6-dioxaoctyl)amine (0.001 mole) are added.

The mixture is agitated for 10 minutes at ambient temperature, then is centrifuged. The clear solution obtained in this manner is analyzed by flame spectrometry.

Solubility measured: 7500 mg/l.
Maximum calculated solubility: 9295 mg/l.
Proportion dissolved: 80%.
Complex formed: $[N(CH_2-CH_2-O-CH_2-CH_2-O-CH_2H_5)_3](WCl_6)$.

Comparative experiment: The operation is effected as above, but without the addition of tris(3,6-dioxaoctyl)amine.

Solubility measured: 200 mg/l.

EXAMPLE 24

Direct Solubilization of Iridium Trichloride in Toluene

The operation is performed as in Example 23, but using the following reagents:

$IrCl_3 = 0.297$ g (0.001 mole)
Tris(3,6-dioxaoctyl)amine = 0.365 g (0.001 mole)
Toluene = 20 cm$^3$.
Solubility measured: 2060 mg/l.
Maximum calculated solubility: 9580 mg/l.
Proportion dissolved: 20%

Comparative experiment. The operation is effected as above, but without the addition of tris(3,6-dioxaoctyl)amine.

Solubility measured: less than 1 mg/l.

EXAMPLE 25

Direct Solubilization of Rhenium Trichloride in Toluene

The operation is performed as in Example 23, but using the following reagents:

$ReCl_3 = 0.292$ g (0.001 mole)
Tris(3,6-dioxaoctyl)amine = 0.365 g (0.001 mole)
Toluene = 20 cm$^3$.
Measured solubility: 2090 mg/l.
Maximum calculated solubility: 9310 mg/l.
Proportion dissolved: 22%.

Comparative experiment. The operation is effected as above, but without the addition of tris(3,6-dioxaoctyl)amine.

Solubility measured: less than 1 mg/l.

EXAMPLE 26

Direct Solubilization of Ruthenium Trichloride in Toluene

The operation is performed as in Example 23, but using the following reagents:
$RuCl_3 = 0.207$ g (0.001 mole)
Tris(3,6-dioxaoctyl)amine = 0.365 g (0.001 mole)
Toluene = 20 cm$^3$.
Solubility measured: 1600 mg/l.
Maximum calculated solubility: 5050 mg/l.
Proportion dissolved: 32%.
Complex formed: $[N(CH_2-CH_2-O-CH_2-CH_2-O-C_2H_5)_3](RuCl_3)$.

Comparative experiment. The operation is effected as above, but without the addition of tris(3,6-dioxaoctyl)amine.
Solubility measured: less than 1 mg/l.

EXAMPLE 27

Direct Solubilization of Molybdenum Pentachloride in Toluene

The operation is performed as in Example 23, but using the following reagents:
$MoCl_5 = 0.273$ g (0.001 mole)
Tris(3,6-dioxaoctyl)amine = 0.365 g (0.001 mole)
Toluene = 20 cm$^3$.
Solubility measured: 80 mg/l.
Maximum calculated solubility: 4800 mg/l.
Proportion dissolved: 2%.

Comparative experiment. The operation is effected as above, but without the addition of tris(3,6-dioxaoctyl)amine.
Solubility measured: 10 mg/l.

EXAMPLE 28

Direct Solubilization of Rhodium Trichloride in Toluene

The operation is performed as in Example 23, but using the following reagents:
$RhCl_3 = 0.209$ g (0.001 mole)
Tris(3,6-dioxaoctyl)amine = 0.365 g (0.001 mole)
Toluene = 20 cm$^3$.
Solubility measured: 683 mg/l.
Maximum calculated solubility: 5150 mg/l.
Proportion dissolved: 13%.

Comparative experiment. The operation is effected as above, but without the addition of tris(3,6-dioxaoctyl)amine.
Solubility measured: less than 1 mg/l.

EXAMPLE 29

Direct Solubilization of Platinum Chloride in Toluene

The operation is performed as in Example 23, but using the following reagents:
$PtCl_2 = 0.266$ g (0.001 mole)
Tris(3,6-dioxaoctyl)amine = 0.365 g (0.001 mole)
Toluene = 20 cm$^3$.
Solubility measured: 9700 mg/l.
Maximum calculated solubility: 9755 mg/l.
Proportion dissolved: 99%.
Complex formed: $[N(CH_2-CH_2-O-CH_2-CH_2-O-C_2H_5)_3](PtCl_2)$.

Comparative experiment. The operation is effected as above, but without the addition of tris(3,6-dioxaoctyl)amine.
Solubility measured: less than 1 mg/l.

EXAMPLE 30

Direct Solubilization of Ruthenium Trichloride in Cyclohexane

Into a 50 ml Erlenmeyer flask, equipped with an ascending cooler and a magnetic agitator, are introduced 20 ml of cyclohexane. Then, 0.207 g of ruthenium trichloride (0.001 mole) and 0.365 g of tris(3,6-dioxaoctyl)amine (0.001 mole) are added.

The mixture is agitated for 10 minutes at ambient temperature, then is centrifuged. The clear solution obtained in this manner is analyzed by flame spectrometry.
Solubility measured: 110 mg/l.
Maximum calculated solubility: 5050 mg/l.
Proportion dissolved: 2%.
Complex formed: $[N(CH_2-CH_2-O-CH_2-CH_2-O-C_2H_5)_3](RuCl_3)$.

Comparative experiment. The operation is carried out as above, without the addition of tris(3,6-dioxaoctyl)amine.
Solubility measured: less than 1 mg/l.

EXAMPLE 31

Direct Solubilization of Iridium Trichloride in Cyclohexane

The operation is performed as in Example 30, but using the following reagents:
$IrCl_3 = 0.299$ g (0.001 mole)
Tris(3,6-dioxaoctyl)amine = 0.365 g (0.001 mole)
Cyclohexane = 20 cm$^3$.
Solubility measured: 4700 mg/l.
Maximum calculated solubility: 9610 mg/l.
Proportion dissolved: 50%.
Complex formed: $[N(CH_2-CH_2-O-CH_2-CH_2-O-C_2H_5)_3](IrCl_3)$.

Comparative experiment. The operation is effected as above, but without the addition of tris(3,6-dioxaoctyl)amine.
Solubility measured: less than 1 mg/l.

EXAMPLE 32

Direct Solubilization of Platinum Chloride in Cyclohexane

The operation is performed as in Example 30, but using the following reagents:
$PtCl_2 = 0.266$ g (0.001 mole)
Tris(3,6-dioxaoctyl)amine = 0.365 g (0.001 mole)
Cyclohexane = 20 cm$^3$.
Solubility measured: 1500 mg/l.
Maximum calculated solubility: 9755 mg/l.
Proportion dissolved: 15%.
Complex formed: $[N(CH_2-CH_2-O-CH_2-CH_2-O-C_2H_5)_3](PtCl_2)$.

Comparative experiment. The operation is effected as above, but without the addition of tris(3,6-dioxaoctyl)amine.
Solubility measured: less than 1 mg/l.

EXAMPLE 33

Direct Solubilization of Rhodium Trichloride in Cyclohexane

The operation is performed as in Example 30, but using the following reagents:
$RhCl_3 = 0.209$ g (0.001 mole)

Tris(3,6-dioxaoctyl)amine = 0.365 g (0.001 mole)
Cyclohexane = 20 cm$^3$.
Solubility measured: 20 mg/l.
Maximum calculated solubility: 5150 mg/l.
Proportion dissolved: 0.4%.

Comparative experiment. The operation is effected as above, but without the addition of tris(3,6-dioxaoctyl)amine.
Solubility measured: less tham 1 mg/l.

EXAMPLE 34

Direct Solubilization of Cadmium Iodide in Methylene Chloride

The operation is performed as in Example 1, but using the following reagents:
$CdI_2$ = 0.366 g (0.001 mole)
Tris(3,6-dioxaheptyl)amine = 0.32 g (0.001 mole)
$CH_2Cl_2$ = 10 cm$^3$.
Solubility measured: 9500 mg/l.
Maximum calculated solubility: 11240 mg/l.
Proportion dissolved: 85%.
Complex formed: $[N(CH_2-CH_2-O-CH_2-CH_2-O-CH_3)_3](CdI_2)$.

Comparative Experiment. The operation is effected as above, but without the addition of tris(3,6-dioxaheptyl)amine.
Solubility measured: less tham 0.5 mg/l.

EXAMPLE 35

Effect of the Size of the Cation on the Degree of Solubilization in Methylene Chloride Three experiments are performed as in Example 1, except that the mixture is agitated for several minutes and then allowed to decant overnight, using the following reagents:

Experiment 1

LiSCN = 0.065 g (0.001 mole).
Tris(3,6-dioxaheptyl)amine = 0.323 g (0.001 mole).
$CH_2Cl_2$ = 10 cm$^3$.

Experiment 2

NaSCN = 0.080 g (0.001 mole).
Tris(3,6-dioxaheptyl)amine = 0.32 g (0.001 mole).
$CH_2Cl_2$ = 10 cm$^3$.

Experiment 3

KSCN = 0.097 g (0.001 mole).
Tris(3,6-dioxaheptyl)amine = 0.32 g (0.001 mole).
$CH_2Cl_2$ = 10 cm$^3$.

Three comparative experiments also are effected as above, but without the addition of tris(3,6-dioxaheptyl)amine.

The results obtained are given in Table I hereinbelow. The complexes formed are:
Experiment 1: $[N(CH_2-CH_2-O-CH_2-CH_2-O-CH_3)_3](LiSCN)$
Experiment 2: $[N(CH_2-CH_2-O-CH_2-CH_2-O-CH_3)_3](NaSCN)$
Experiment 3: $[N(CH_2-CH_2-O-CH_2-CH_2-O-CH_3)_3](KSCN)$.
The proportions dissolved are as follows:
Experiment 1: 98%
Experiment 2: 82%
Experiment 3: 79%.

TABLE I

| Experiment | Salt | With tris (3,6-dioxaheptyl)amine | | Without tris (3,6-dioxaheptyl) amine |
|---|---|---|---|---|
| | | Solubility Measured | Maximum Calculated Solubility | Solubility Measured |
| 1 | LiSCN | 680 mg/l | 694 mg/l | <1 mg/l |
| 2 | NaSCN | 1,800 mg/l | 2,300 mg/l | <1 mg/l |
| 3 | K SCN | 3,100 mg/l | 3,910 mg/l | <1 mg/l |

EXAMPLE 36

Effect of Temperature on the Degree of Solubilization of Lithium Thiocyanate in Toluene 10 cm$^3$ of a 0.1 M tris(3,6-dioxaheptyl)amine solution in toluene are agitated at ambient temperature with 1.1 millimole of powdered lithium thiocyanate.

After decanting the solution, the toluene phase is analyzed. It is determined by infrared analysis that the tris(3,6-dioxaheptyl)amine has almost totally disappeared from the solution. This may be explained by the formation of the complex:

(LiSCN)[tris(3,6-dioxaheptyl)amine]

which has a very low solubility in toluene at ambient temperature.

The above procedure is repeated, except that the mixture is agitated 60° C. The solution becomes clear and infrared analysis shows that all of the above-mentioned complex is found in the toluene phase.

EXAMPLE 37

Indirect Solubilization of Ammonium Thiocyanate 0.455 g (0.001 mole) of tris(3,6,9-trioxadecyl)amine is dissolved in 10 ml of anhydrous methanol, then 0.076 g (0.001 mole) of ammonium thiocyanate is introduced. The mixture is agitated for 1 hour at ambient temperature. The methanol is then slowly evaporated and the mixture obtained is taken up in 20 cm$^3$ of methylene chloride. The solution is filtered and the solvent is evaporated. An orange colored liquid complex is obtained having a sulfur content of 4.8%. (The maximum calculated content is 6.03%).

The complex corresponds to the formula:

$[N(CH_2-CH_2-O-CH_2-CH_2-O-CH_2-CH_2-O-CH_3)_3](NH_4SCN)$.

EXAMPLE 38

Indirect Solubilization of Lithium Chloride in Various Solvents 1.6 of tris(3,6-dioxaheptyl)amine (0.005 mole) is dissolved in 30 ml of anhydrous methanol. Into the solution thus obtained, 0.22 g (0.005 mole) of anhydrous lithium chloride is introduced. The mixture is agitated for 1 hour at ambient temperature. The methanol is then slowly evaporated and the mixture obtained is taken up in 20 cm$^3$ methylene chloride. The solution is filtered and the solvent is evaporated. An orange colored liquid is obtained, which is the lithium chloride-tris(3,6-dioxaheptyl)amine complex having lithium and chloride contents as follows:
Li$^+$: 1.7% (theoretical: 1.91%)
Cl$^-$: 8.6% (theoretical: 9.71%)

and a formula of [N(CH$_2$—CH$_2$—O—CH$_2$—CH$_2$—O—CH$_3$)$_3$](LiCl).

The orange colored liquid is particularly soluble in chlorobenzene, chloroform and dimethylsulfoxide.

EXAMPLE 39

Indirect Solubilization of Lithium Chloride 0.455 g (0.001 mole) of tris(3,6,9-trioxadecyl)amine is dissolved in 10 ml of anhydrous methanol and 0.042 g (0.001 mole) of dehydrated lithium chloride is then introduced. The mixture is agitated for 1 hour at ambient temperature. The methanol is then slowly evaporated and the mixture thus obtained is taken up in 20 cm$^2$ of methylene chloride. The solution is filtered and the solvent is evaporated. An orange colored liquid is obtained, representing the complex:

[N(CH$_2$—CH$_2$—O—CH$_2$—CH$_2$—O—CH$_2$—CH$_2$—O—CH$_3$)$_3$](LiCl)

having the following lithium and chlorine contents:
Li$^+$: 1.03% (theoretical: 1.41%)
Cl$^-$: 5.3% (theoretical: 7.16%).

This complex is soluble in chlorobenzene, dimethylsulfoxide, N-methylpyrrolidone, and chloroform.

EXAMPLE 40

Effect of the Sequestering Agent Content on the Rate of Extraction of Cesium Picrate An aqueous solution containing 0.1 mole/l of cesium hydroxide and 0.0015 mole/l of picric acid is prepared.

A solution in methylene chloride of 0.007 mole/l of tris(3,6-dioxaheptyl)amine and a solution of 0.007 mole/l of tris(3,6,9-trioxadecyl)amine in methylene chloride are also prepared.

Equal volumes of each of the solutions of the sequestering agents are mixed with the cesium picrate solution.

In the case of tris(3,6-dioxaheptyl)amine, an extraction of 22% of cesium picrate is observed.

In the case of tris(3,6,9-trioxadecyl)amine, an extraction of 60% is obtained.

A comparative experiment without sequestering agent gives no extraction.

EXAMPLE 41

Effect of the Sequestering Agent Content on the Rate of Extraction of Sodium Picrate The operation is as follows: An aqueous solution A containing 1 mole/l of sodium hydroxide and 0.00021 mole/l of picric acid is prepared. Similarly, nine solutions B of sequestering agents according to the invention, in methylene chloride, are prepared by varying the nature of the sequestering agent and its concentration.

Nine experiments are then executed by mixing equal volumes of solutions A and B and measuring the percentage of sodium picrate extracted, i.e. the percent passing from the aqueous phase into the methylene chloride phase.

The results obtained are given in Table II below.

TABLE II

| Experiment | Sequestering Agent | Concentration of the Sequestering Agent mole/l | Sodium Picrate Extracted |
|---|---|---|---|
| 1 | tris(3,6-dioxaheptyl)amine | 8.85 × 10$^{-5}$ | 28% |
| 2 | " | 2.62 × 10$^{-4}$ | 51% |

TABLE II-continued

| Experiment | Sequestering Agent | Concentration of the Sequestering Agent mole/l | Sodium Picrate Extracted |
|---|---|---|---|
| 3 | " | 2.6 × 10$^{-3}$ | 92.5% |
| 4 | tris(3,6-dioxaoctyl)amine | 8.08 × 10$^{-5}$ | 11% |
| 5 | " | 2.33 × 10$^{-4}$ | 17% |
| 6 | " | 2.33 × 10$^{-3}$ | 54% |
| 7 | tris(3,6-dioxadecyl)amine | 7.01 × 10$^{-5}$ | 8% |
| 8 | " | 2 × 10$^{-4}$ | 12.5% |
| 9 | " | 2 × 10$^{-3}$ | 42.5% |

It has been found that the amount extracted increases with the amount of sequestering agent used.

A comparative experiment without the addition of a sequestering agent is effected; the percent of sodium picrate extracted is zero.

EXAMPLE 42

Effect of the Nature of the Sequestering Agent on the Rate of Extraction

The operation is as follows: An aqueous solution A containing 0.1 mole/l of sodium hydroxide and 0.0007 mole/l of picric acid is prepared. The solution is agitated for 3 hours. In the same manner, two other solutions A are prepared by replacing sodium hydroxide with potassium hydroxide in the one case and cesium hydroxide in the other.

Two solutions B are then prepared, one with 0.0007 mole/l tris(3,6-dioxaheptyl)amine in methylene chloride, the other with the same amount of tris(3,6,9-trioxadecyl)amine in methylene chloride.

Six experiments are performed by mixing intimately for 1 minute equal volumes of each of the three solutions A with each of the two solutions B and by measuring after decantation the percentage of the picrate extracted, i.e. the percent passing from the aqueous phase into the methylene chloride phase.

The results obtained are given in Table III.

TABLE III

| Salt to be extracted | Tris(3,6-dioxaheptyl)-amine | Tris(3,6,9-trioxadecyl)-amine |
|---|---|---|
| Experiment 1 and 2 Pi$^-$ Na$^+$ | 23% | 13% |
| Experiment 3 and 4 Pi$^-$ K$^+$ | 18% | 29% |
| Experiment 5 and 6 Pi$^-$ Cs$^+$ | 7% | 19% |

In a similar manner, three comparative experiments are effected by mixing the four solutions A with equal volumes of methylene chloride containing no sequestering agent: the extraction percentages of the different picrates are zero.

EXAMPLE 43

Extraction of Barium Picrate in Aqueous Solution

The operation is performed as follows: An aqueous solution A containing 0.1 mole/l of barium hydroxide and 0.014 mole/l of picric acid is prepared. The solution is agitated for 3 hours. Two solutions B are also prepared, one containing 0.007 mole/l of tris(3,6-dioxaheptyl)amine, the other 0.007 mole/l of tris(3,6,9-trioxadecyl)amine, in methylene chloride.

Equal volumes of solution A and each of the solutions B are mixed intimately for 1 minute. The percentage of the picrate extracted is measured after decantation (i.e. the percent of picrate passing from the aqueous phase into the methylene chloride phase).

With tris(3,6-dioxaheptyl)amine, 75.5% barium picrate is extracted; with tris(3,6,9-trioxadecyl)amine the proportion is 77.5%.

Without the sequestering agent, the percent of extraction is zero.

EXAMPLE 44

Direct Solubilization of Lead Thiocyanate in Methanol and in Acetonitrile

Two experiments are performed as in Example 1, except that the mixture is agitated for a few minutes and allowed to decant overnight, using the reagents indicated below:

Experiment 1

$Pb(SCN)_2 = 0.323$ g (0.001 mole).
Tris(3,6,9-trioxadecyl)amine = 0.455 g (0.001 mole).
Methanol = 10 cm$^3$.
Solubility measured: 12900 mg/l.
Maximum calculated solubility: 20720 mg/l.
Proportion dissolved: 62%.

Comparative example. The operation is effected as above, but without the addition of tris(3,6,9-trioxadecyl)amine.
Solubility measured: 250 mg/l.

Experiment 2

$Pb(SCN)_2 = 0.323$ g (0.001 mole).
Tris(3,6,9-trioxadecyl)amine = 0.455 g (0.001 mole).
Acetonitrile = 10 cm$^3$.
Solubility measured: 500 mg/l.
Maximum solubility calculated: 20720 mg/l.
Proportion dissolved: 2%.

After a decantation of 3 days, the following results are obtained:
Solubility measured: 2800 mg/l
Proportion dissolved: 13.5%.

Comparative experiment. The operation is effected as above, but without the addition of tris(3,6,9-trioxadecyl)amine.
Solubility measured: less tham 10 mg/l.

EXAMPLE 45

Direct Solubilization of Lead Acetate in Acetonitrile and Methylene Chloride

Two experiments are performed as in Example 1, except that the mixture is agitated for a few minutes and the allowed to decant overnight, using the reagents indicated below:

Experiment 1

$(CH_3COO)_2Pb = 0.325$ g (0.001 mole).
Tris(3,6,9-trioxadecyl)amine = 0.455 g (0.001 mole).
Acetonitrile = 10 cm$^3$.
Solubility measured: 7750 mg/l.
Maximum solubility calculated: 20720 mg/l.
Proportion dissolved: 37.5%.

Comparative experiment. The operation is effected as above, but without the addition of tris(3,6,9-trioxadecyl)amine.
Solubility measured: 65 mg/l.

Experiment 2

$(CH_3COO)_2Pb = 0.325$ g (0.001 mole).
Tris(3,6-dioxaheptyl)amine = 0.32 g (0.001 mole).
Methylene chloride = 10 cm$^3$.
Solubility measured: 2000 mg/l.
Maximum calculated solubility: 20720 mg/l.
Proportion dissolved: 10%.

Comparative experiment. The operation is effected as above, but without the addition of tris(3,6-dioxaheptyl)amine.
Solubility measured: less than 15 mg/l.

Examples 46 to 51 below describe the preparation of representative sequestering agents of the invention, namely tris(3,6-dioxaheptyl)amine, tris(3,6,9-trioxadecyl)amine, tris(3,6-dioxadecyl)amine, tris[3-oxabutyl]amine, tris(3,6,9,12-tetraoxatridecyl)amine and tris(3,6,9,12,15,18-hexaoxanonadecyl)amine. All of the other sequestering agents envisioned by the present invention may be prepared by similar processes.

EXAMPLE 46

Preparation of Tris(3,6-dioxaheptyl)amine (a) Preparation of sodium 2-methoxyethanolate Into a one liter three-necked flask, equipped with a mechanical agitator, a thermometer, and a cooler, 380 g of 2-methoxyethanol (5 moles) are introduced. 23 g of sodium (1 mole) are added over a three hour period, while maintaining the temperature of the mixture at 40° C.

(b) Synthesis of tris(3,6-dioxaheptyl)amine

To the mixture thus obtained, 51.6 g of tris(2-chloroethyl)amine hydrochloride (0.215 mole) are added. The mixture is then heated at the reflux temperature of the 2-methoxyethanol (125° C.) for 12 hours and then the solvent is removed by distillation under reduced pressure. The excess sodium 2-methoxyethanolate is neutralized by the addition of 11.6 cm$^3$ aqueous HCl (10 N). The sodium chloride is filtered off and the solution is distilled.

Tris(3,6-dioxaheptyl)amine distills between 165° C. and 180° C. under a pressure of 0.5 mmHg. 49 g of the product are thus obtained, representing a yield of 70%.

EXAMPLE 47

Preparation of tris(3,6-dioxadecyl)amine

Into a 1 liter three-necked flask, equipped as described in Example 1, 590 g of 3-oxaheptan-1-ol (i.e., the butyl monoether of ethylene glycol) are introduced. 40 g of sodium hydroxide in pellet form are added and the mixture is heated to 120° C. Sodium 3-oxaheptan-1-olate and water are formed, with the latter being removed by distillation.

When all of the water of the reaction has been eliminated, 55 g of tris(2-chloroethyl)amine hydrochloride are introduced. The mixture is heated at 130° C. for 5 hours, then cooled. Excess sodium alcoholate is then neutralized with a 10% aqueous solution of hydrochloric acid. The 3-oxaheptan-1-ol is removed by distillation and the sodium chloride is removed by filtration. The desired product, tris(3,6-dioxadecyl)amine, is distilled (192° C. under 0.1 mmHg).

EXAMPLE 48

Preparation of Tris(3,6,9-trioxadecyl)amine

To a three-necked 1 liter flask equipped with a mechanical agitator, a condenser and a thermometer, and containing 600 g of the monomethyl ether of diethylene glycol (i.e. 3,6-dioxaheptan-1-ol), corresponding to 5 moles, 23 g of sodium (1 mole) are introduced in small fractions to form sodium 3,6-dioxaheptan-1-olate.

When the sodium has been completely transformed, 51.8 g of tris(2-chloroethyl)amine hydrochloride (0.215 mole) are added. The mixture is heated at 130° C. for 8 hours under agitation, then is cooled and the excess sodium alcoholate is neutralized by a 10% aqueous hydrochloric acid solution. The 3,6-dioxaheptan-1-ol is eliminated by distillation at 130° C. under a pressure of 20 mmHg. The mixture thus obtained is filtered to eliminate sodium chloride and the product is then distilled. In this manner, 83 g of tris(3,6,9-trioxadecyl)amine are obtained, distilling at 189° C. under 0.1 mmHg.

EXAMPLE 49

Preparation of Tris(3-oxabutyl)amine

To a three-necked 1 liter flask equipped with a mechanical agitator, a condenser and a thermometer, and containing 244 g of methanol, 23 g of sodium are added. A solution of 30 g (0,125 mole) of tris(chloroethyl)amine hydrochloride in 150 g of methanol are added. The mixture is heated at the reflux temperature for 4 hours, then is cooled and the excess methylate is neutralized by 75 g of concentrated HCl. The methanol is concentrated. The aqueous layer is extracted with 2×100 g of dichloromethane. After evaporation of dichloromethane, the desired product, tris(3-oxabutyl)amine is distilled. 18 g are obtained (R=75,7%).

EXAMPLE 50

Preparation of Tris(3,6,9,12-tetraoxatridecyl)amine

To a three-necked 3 liters flask equipped with a mechanical agitator, a condenser and a thermometer, and containing 1640 g (10 moles) of monomethylether of triethylene glycol 115 g (5 moles) of sodium are introduced. The resultant suspension is maintained at 80° C. and a solution of 241 g (1 mole) of tris($\beta$ chloroethyl)amine hydrochloride in 492 g monomethyl ether of triethylene glycol are added.

The mixture is maintained at 120°-130° C. for 12 hours. The main part of monomethyl ether of triethylene glycol is eliminated by distillation under vacuum. The residue is then cooled and 2000 ml of acidified dichloromethane are added, and the sodium chloride is remoded by filtration. The monomethyl ether of triethylene glycol and the dichloromethane are eliminated by distillation of the filtrate. The resultant tertiary amine is purified with a silica column. 437 g of desired product are obtained (R=74,7%).

EXAMPLE 51

Preparation of tris(3,6,9,12,15,18-hexaoxanonadecyl)amine

In the apparatus of example 50, 69 g (3 moles) of sodium are dissolved in 1500 g of monomethyl ether of pentaethylene glycol at 80° C. 120 g (0,5 mole) of tris($\beta$ chloroethyl)amine hydrochloride in 600 g of monomethyl ether of pentaethylene glycol are added to the resultant suspension. The mixture is headed a 125°-140° C. for 15 hours, then cooled and the sodium chloride is removed by filtration. The monomethyl ether of pentaethylene glycol is eliminated by distillation at 300° C. under a pressure of 0,5 mmHg.

The tertiary amine is filtrated and purified with a silica column.

331 g of desired product are obtained (R=78%).

EXAMPLE 52

Effect of the Nature of the Sequestering Agent on the Rate of Extraction

The operation is a follows: An aqueous solution A containing 1 mole/l of sodium hydroxyde and 0,005 mole/l of picric acid is prepared. An aqueous solution A' containing 1 mole/l of potassium hydroxyde and 0,005 mole/l of picric acid is prepared.

Five solutions B are then prepared with five different sequestering agents (0,005 mole/l) in methylene chloride.

Ten experiments are performed by mixing 10 cm³ of each of the five solution B with each of the solutions A and A' and by measuring the percentage of the sodium and potassium picrate extracted, i.e. the percent passing from the aqueous phase into the methylene chloride phase. The results are given in Table IV.

TABLE IV

| Experiment | Sequestering Agent | Sodium picrate extracted % | Potassium picrate extracted % |
|---|---|---|---|
| 1–2 | tris(3,6 dioxaheptyl) amine | 40,5 | 35 |
| 3–4 | tris(3,6 dioxaoctyl) amine | 15,5 | 25,5 |
| 5–6 | tris(3,6,9 trioxadecyl) amine | 22,5 | 45,5 |
| 7–8 | tris(3,6,9,12 tetraoxatridecyl) amine | 25 | 55 |
| 9–10 | tris(3,6,9,12,15,18 hexaoxanonadecyl) amine | 22 | 53 |

EXAMPLE 53

Direct Solubilization of Alkaline Thiocyanates in Methylene Chloride

Three experiments are performed as in Example 1 allowing to decant overnight.

Experiment 1

Li SCN=0,065 g (0,001 mole).
Tris(3-oxabutyl)amine=0,191 g (0,001 mole).
$CH_2Cl_2$=10 cm³.
Solubility measured=690 mg/l.
Maximum calculated solubility=694 mg/l.
Proportion dissolved=99,5%.

Comparative experiment. The operation is effected as above, but without the addition of tris(3-oxabutyl)amine
Solubility measured<1 mg/l.

Experiment 2

Na SCN=0,081 g (0,001 mole).
Tris(3-oxabutyl)amine=0,191 g (0,001 mole).
$CH_2Cl_2$—10 cm³.
Solubility measured=2150 mg/l.
Maximum calculated solubility=2300 mg/l.
Proportion dissolved=93.5%.

Comparative experiment. The operation is effected as above, but without the addition of tris(3-oxabutyl)amine.

Solubility measured < 1 mg/l.

Experiment 3

KSCN = 0,097 g (0,001 mole).
Tris(3-oxabutyl)amine = 0,191 g (0,001 mole).
$CH_2Cl_2$ = 10 cm$^3$.
Solubility measured = 490 mg/l.
Maximum calculated solubility = 3910 mg/l.
Proportion dissolved = 12.5%.

Comparative experiment. The operation is effected as above, but without the addition of tris(3-oxabutyl)amine.

Solubility measured < 1 mg/l.

EXAMPLE 54

Direct Solubilization of Iron Chloride in Methylene Chloride

The operation is performed as in Example 1, but using the following reagents:
$FeCl_3$ = 0,162 g
Tris(3,6,dioxaheptyl)amine = 0,32 g.
$CH_2Cl_2$ = 20 cm$^3$.
Solubility measured = 2720 mg/l.
Maximum calculated solubility = 2790 mg/l.
Proportion dissolved = 97%.

Comparative experiment. The operation is effected as above, but without tris(3,6 dioxaheptyl)amine.

Solubility measured = 1400 mg/l.

EXAMPLE 55

Direct Solubilization of Iron Chloride in 1,2 dichloroethane

The operation is performed as in Example 1, but using the following reagents:
$FeCl_3$ = 0,162 g
Tris(3,6 dioxaheptyl)amine = 0,32 g
$C_2H_4Cl_2$ = 20 cm$^3$.
Solubility measured = 2700 mg/l.
Maximum calculated solubility = 2790 mg/l.
Proportion dissolved = 97%.

Comparative experiment. The operation is effected as above, but without tris(3,6 dioxaheptyl)amine.

Solubility measured = 1980 mg/l.

EXAMPLE 56

Direct Solubilization of Antimony Chloride in Methylene Chloride

The operation is performed as in Example 1, but using the following reagents:
$SbCl_3$ = 0,228 g
Tris(3,6 dioxaheptyl)amine = 0,32 g
$CH_2Cl_2$ = 20 cm$^3$.
Solubility measured = 5950 mg/l.
Maximum calculated solubility = 6090 mg/l.
Proportion dissolved = 98%.

Comparative experiment. The operation is effected as above, but without tris(3,6 dioxaheptyl)amine.

Solubility measured = 5650 mg/l.

EXAMPLE 57

Direct Solubilization of Sodium Methoxyphenate in Methylene Chloride

The operation is performed as in Example 1, but using the following reagents:
Sodium methoxyphenate = 0,146 g
Tris(3,6 dioxaheptyl)amine = 0,32 g
$CH_2Cl_2$ = 20 cm$^3$.
Solubility measured = 380 mg/l.
Maximum calculated solubility = 1150 mg/l.
Proportion dissolved = 33%.

Comparative experiment. The operation is effected as above, but without tris(3,6 dioxaheptyl)amine.

Solubility measured < 10 mg/l.

EXAMPLE 58

Direct Solubilization of Lanthanum Nitrate in Methylene Chloride

Into a 50 ml Erlenmeyer flask, equipped with an ascending cooler and a magnetic agitator, are introduced 20 ml of anhydrous and purified methylene chloride. Then, 0,001 mole of lanthanum nitrate and 0,001 mole of tris(3,6 dioxaheptyl)amine are added.

The mixture is agitated for 1 hour at ambient temperature, then is centrifuged. The clear solution obtained in this manner is analysed by X fluorescence.

La $(NO_3)_3$, $6H_2O$ = 0.433 g.
Tris(3,6 dioxaheptyl)amine = 0.32 g.
$CH_2Cl_2$ = 20 cm$^3$.
Solubility measured = 1440 mg/l.
Maximum calculated solubility = 6950 mg/l.
Proportion dissolved = 21%.

Comparative experiment. The operation is effected as above, but without tris(3,6 dioxaheptyl)amine.

Solubility measured = 10 mg/l.

EXAMPLE 59

Direct Solubilization of Cerium Nitrate in Methylene Chloride

The operation is performed as in Example 58 but using the following reagents:
Ce $(NO_3)_3$, $6H_2O$ = 0.434 g
Tris(3,6 dioxaheptyl)amine = 0.32 g
$CH_2Cl_2$ = 20 cm$^3$.
Solubility measured = 1740 mg/l.
Maximum calculated solubility = 7010 mg/l.
Proportion dissolved = 25%.

Comparative experiment. The operation is effected as above, but without using tris(3.6 dioxaheptyl)amine.

Solubility measured < 10 mg/l.

EXAMPLE 60

Direct Solubilization of Europium Nitrate in Methylene Chloride

The operation is performed as in Example 58 but using the following reagents:
Eu $(NO_3)_3$, $6H_2O$ = 0.446 g
Tris(3,6 dioxaheptyl)amine = 0,32 g
$CH_2Cl_2$ 20 cm$^3$.
Solubility measured = 250 mg/l.
Maximum calculated solubility = 7600 mg/l.
Proportion dissolved = 3%.

Comparative experiment. The operation is effectued as above, but without tris(3.6 dioxaheptyl)amine.

Solubility measured = 50 mg/l.

EXAMPLE 61

Direct Solubilization of Thorium Nitrate in Methylene Chloride

The operation is performed as in Example 58 but using the following reagents:
Th (NO$_3$)$_4$, 4H$_2$O = 0,552 g
Tris(3,6 dioxaheptyl)amine = 0,32 g
CH$_2$Cl$_2$ = 20 cm$^3$.
Solubility measured = 5500 mg/l.
Maximum calculated solubility = 11.600 mg/l.
Proportion dissolved = 47%.

Comparative experiment. The operation is effected as above, but without using tris(3,6 dioxaheptyl)amine.
Solubility measured <10 mg/l.

EXAMPLE 62

Direct Solubilization of Uranyle Nitrate in Methylene Chloride

The operation is performed as in Example 58 but using the following reagents:
UO$_2$ (NO$_3$)$_2$, 6H$_2$O = 0,502 g
Tris(3,6 dioxaheptyl)amine = 0,32 g
CH$_2$Cl$_2$ = 20 cm3.
Solubility measured = 6100 mg/l.
Maximum calculated Solubility = 11.900 mg/l.
Proportion dissolved = 51%.

Comparative experiment. The operation is effectued as above but without using tris(3.6 dioxaheptyl)amine.
Solubility measured <10 mg/l.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for solubilizing an organic or mineral salt in an organic solvent in which the organic or mineral salt is initially not soluble, or for increasing the solubility of an organic or mineral salt in an organic solvent, said process comprising contacting said organic or mineral salt of the formula A$^-$M$^+$, wherein A$^-$ is a mineral or organic anion and M$^+$ is a cation selected from the group consisting of the cation NH$_4^+$ and its derivatives, and the cations derived from the metals of the groups I$_A$, II$_A$, III$_A$, IV$_A$, V$_A$, VI$_A$, VII$_A$, VIII, I$_B$, II$_B$, III$_B$, IV$_B$ and V$_B$ of the periodic table, with at least one sequestering agent, said sequestering agent being soluble in said organic solvent and having the formula:

$$N[CHR_1-CHR_2-O-(CHR_3-CHR_4-O)_n-R_5]_3 \quad (I)$$

wherein n is an integer from 0 to 10 inclusive; R$_1$, R$_2$, R$_3$ and R$_4$, which can be the same or different, are each a hydrogen atom or an alkyl radical having 1 to 4 carbon atoms; R$_5$ is a radical selected from the group consisting of an alkyl radical having 1 to 12 carbon atoms, a cycloalkyl radical having 3 to 12 carbon atoms, a phenyl radical, a radical of the formula

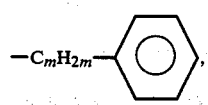

and a radical of the formula

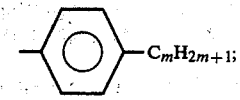

and m is an integer from 1 to 12 inclusive; said sequestering agent of formula (I) and said organic or mineral salt forming a complex of the formula:

$$[N-[CHR_1-CHR_2-O-(CHR_3-CHR_4-O)- _n-R_5]_3]_y (M^+A^-) \quad (II)$$

wherein y is greater than or equal to 1 and less than or equal to 3, and R$_1$, R$_2$, R$_3$, R$_4$, R$_5$, n, M$^+$ and A$^-$ are defined as above, said complex of formula (II) being soluble in said organic solvent.

2. The process of claim 1 comprising a single stage wherein the organic or mineral salt in anhydrous form is contacted with the sequestering agent of formula (I) in solution in said organic solvent.

3. The process of claim 1 comprising a single stage wherein the organic or mineral salt in an aqueous solution is contacted with the sequestering agent of formula (I) in solution in said organic solvent.

4. The process of claim 1 wherein, in a first stage, the mineral or organic salt in solution in a third solvent is contacted with the sequestering agent of formula (I) in solution in said third solvent; in a second stage, said third solvent is eliminated; and in a third stage, the product resulting from the second stage is contacted with said organic solvent.

5. The process of claim 1 wherein, in a first stage, the organic or mineral salt in anhydrous form is contacted with the sequestering agent of formula (I) in the absence of solvent; and, in a second stage, the product resulting from the first stage is contacted with said organic solvent.

6. The process of claim 1, 2, 3, 4 or 5 wherein, in formula (I), R$_1$, R$_2$, R$_3$ and R$_4$, which can be the same or different, are each a hydrogen atom or a methyl radical.

7. The process of claim 1, 2, 3, 4 or 5 wherein, in formula (I), n is an integer from 0 to 6 inclusive.

8. The process of claim 1, 2, 3, 4 or 5 wherein, in formula (I), R$_5$ is an alkyl radical having 1 to 4 carbon atoms.

9. The process of claim 1, 2, 3, 4 or 5, wherein, in formula (I), R$_1$, R$_2$, R$_3$ and R$_4$, which can be the same or different, are each a hydrogen atom or a methyl radical; n is an integer from 0 to 6 inclusive; and R$_5$ is an alkyl radical having 1 to 4 carbon atoms.

10. The process of claim 9 wherein the sequestering agent of formula (I) is tris(3,6-dioxaheptyl)amine.

11. The process of claim 9 wherein the sequestering agent of formula (I) is tris(3,6,9-trioxadecyl)amine.

12. The process of claim 9 wherein the sequestering agent of formula (I) is tris(3,6-dioxaoctyl)amine.

13. The process of claim 9 wherein the sequestering agent of formula (I) is tris(3,6,9-trioxaundecyl)amine.

14. The process of claim 9 wherein the sequestering agent of formula (I) is tris(3,6-dioxanonyl)amine.

15. The process of claim 9 wherein the sequestering agent of formula (I) is tris(3,6,9-trioxadodecyl)amine.

16. The process of claim 9 wherein the sequestering agent of formula (I) is tris(3,6-dioxadecyl)amine.

17. The process of claim 9 wherein the sequestering agent of formula (I) is tris(3,6,9-trioxatridecyl)amine.

18. The process of claim 9 wherein the sequestering agent of formula (I) is tris(3-oxabutyl)amine.

19. The process of claim 9 wherein the sequestering agent of formula (I) is tris(4-methyl-3,6-dioxaheptyl)amine.

20. The process of claim 9 wherein the sequestering agent of formula (I) is tris(2,4-dimethyl-3,6-dioxaheptyl)amine.

21. The process of claim 1 wherein the cation $M^+$ is selected from the group consisting of the cation $NH_4^+$, the cations $RNH_3^+$ wherein R is an alkyl radical or an aryl radical, and the cations derived from a metal selected from the group consisting of Li, Na, K, Rb, Cs, Mg, Ca, Sr, Ba, Sc, Y, La, a member of the lanthanide series, Ac, a member of the actinide series, Ti, Zr, Hf, V, Nb, Ta, Cr, Mo, W, Mn, Tc, Re, Fe, Co, Ni, Ru, Rh, Pd, Os, Ir, Pt, Cu, Ag, Au, Zn, Cd, Hg, Al, Ga, In, Tl, Ge, Sn, Pb, Sb and Bi.

22. The process of claim 1 wherein the anion $A^-$ is selected from the group consisting of $SCN^-$, $O=C=N^-$, $Cl^-$, $Br^-$, $I^-$, $F^-$, $CN^-$, $SH^-$, $S^{--}$, $OH^-$, $HSO_3^-$, $ClO_4^-$, $BrO_4^-$, $NH_2^-$, $NO_3^-$, $NO_2^-$, $BF_4^-$, $BrO^-$, $ClO^-$, $BH_4^-$, $SO_3^{--}$, $PO_3^{-3}$, $CO_3^{--}$, $SO_4^{--}$, $ClO_3^-$, $BrO_3^-$, $H^-$ and $AlH_4^-$.

23. The process of claim 1 wherein the anion $A^-$ is selected from the group consisting of the anions derived from alcohols, phenols, thiols, thiophenols, acids, amines, amides, organic compounds with mobile hydrogen, and silanols.

24. The process of claim 1 wherein said organic solvent is selected from the group consisting of hexane, cyclohexane, benzene, toluene, o-xylene, m-xylene, p-xylene, chlorobenzene, o-dichlorobenzene, 1,2,4-trichlorobenzene, chloroform, methylene chloride, carbon tetrachloride, 1,2-dichloroethane, 1,1,1-trichloroethane, 1,1,2-trichloroethane, 1,2,2-trichloro-1,1,2-trifluoroethane, perchloroethylene, acetone, acetonitrile, dimethylformamide, N-methylpyrrolidone, dimethylacetamide, hexamethylphosphorotriamide, dimethylsulfoxide, sulfolane, methanol, ethanol and isopropanol.

25. The process of claim 1 wherein the contacting is effected at a temperature of between about $-50°$ C. and about $250°$ C.

26. The process of claim 1 wherein the sequestering agent of formula (I) is used in an amount such that the molar ratio of the sequestering agent to the $A^-M^+$ salt is between about 0.001 and about 50.

27. A complex of the formula:

$$[N[CHR_1—CHR_2—O—(CHR_3—CHR_4—O)\text{-}_n—R_5]_3]_y(M^+A^-) \quad (II)$$

wherein y is a number from 1 to 3 inclusive; n is an integer from 0 to 10 inclusive; $R_1$, $R_2$, $R_3$ and $R_4$, which can be the same or different, are each a hydrogen atom or an alkyl radical having 1 to 4 carbon atoms; $R_5$ is a radical selected from the group consisting of an alkyl radical having 1 to 12 carbon atoms, a cycloalkyl radical having 3 to 12 carbon atoms, a phenyl radical, a radical of the formula

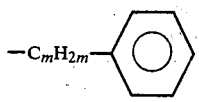

and a radical of the formula

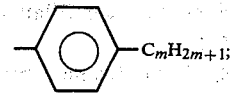

m is an integer from 1 to 12 inclusive; $A^-$ is an organic or mineral anion; and $M^+$ is a cation selected from the group consisting of the cation $NH_4^+$ and its derivatives and the cations derived from the metals of the groups $I_A$, $II_A$, $III_A$, $IV_A$, $V_A$, $VI_A$, $VII_A$, VIII, $I_B$, $II_B$, $III_B$, $IV_B$ and $V_B$ of the periodic table.

28. A complex of claim 27 wherein $R_1$, $R_2$, $R_3$ and $R_4$, which can be the same or different, are each a hydrogen atom or a methyl radical.

29. A complex of claim 27 wherein n is an integer from 0 to 6 inclusive.

30. A complex of claim 27 wherein $R_5$ is an alkyl radical having 1 to 4 carbon atoms.

31. A complex of claim 27 wherein $R_1$, $R_2$, $R_3$ and $R_4$, which can be the same or different, are each a hydrogen atom or a methyl radical; n is an integer from 0 to 6 inclusive; and $R_5$ is an alkyl radical having 1 to 4 carbon atoms.

32. A complex of claim 31, having the formula:

[N—(CH$_2$—CH$_2$—O—CH$_2$—CH$_2$—O—CH$_3$)$_3$]$_y$ (A$^-$M$^+$).

33. A complex of claim 31, having the formula:

[N—(CH$_2$—CH$_2$—O—CH$_2$—CH$_2$—O—CH$_2$—CH$_2$—O—CH$_3$)$_3$]$_y$ (A$^-$M$^+$).

34. A complex of claim 31, having the formula:

[N—(CH$_2$—CH$_2$—O—CH$_2$—CH$_2$—O—C$_2$H$_5$)$_3$]$_y$ (A$^-$M$^+$).

35. A complex of claim 31, having the formula:

[N—(CH$_2$—CH$_2$—O—CH$_2$—CH$_2$—O—CH$_2$—CH$_2$—O—C$_2$H$_5$)$_3$]$_y$ (A$^-$M$^+$).

36. A complex of claim 31, having the formula:

[N—(CH$_2$—CH$_2$—O—CH$_2$—CH$_2$—O—C$_3$H$_7$)$_3$]$_y$ (A$^-$M$^+$).

37. A complex of claim 31, having the formula:

[N—(CH$_2$—CH$_2$—O—CH$_2$—CH$_2$—O—CH$_2$—CH$_2$—O—C$_3$H$_7$)$_3$]$_y$ (A$^-$M$^+$).

38. A complex of claim 31, having the formula:

[N—(CH$_2$—CH$_2$—O—CH$_2$—CH$_2$—O—C$_4$H$_9$)$_3$]$_y$ (A$^-$M$^+$).

39. A complex of claim 31, having the formula:

[N—(CH$_2$—CH$_2$—O—CH$_2$—CH$_2$—O—CH$_2$—CH$_2$—O—C$_4$H$_9$)$_3$]$_y$ (A$^-$M$^+$).

40. A complex of claim 31, having the formula:

[N—(CH$_2$—CH$_2$—O—C$_4$H$_9$)$_3$]$_y$ (A$^-$M$^+$).

41. A complex of claim 31, having the formula:

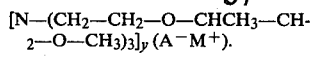

42. A complex of claim 31, having the formula:

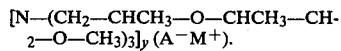

43. A complex of claim 27, 28, 29, 30 or 31 wherein the cation $M^+$ is selected from the group consisting of the cation $NH_4^+$, the cations $RNH_3^+$ wherein R is an alkyl radical or an aryl radical, and the cations derived from a metal selected from the group consisting of Li, Na, K, Rb, Cs, Mg, Ca, Sr, Ba, Sc, Y, La, a member of the lanthanide series, Ac, a member of the actinide series, Ti, Zr, Hf, V, Nb, Ta, Cr, Mo, W, Mn, Tc, Re, Fe, Co, Ni, Ru, Rh, Pd, Os, Ir, Pt, Cu, Ag, Au, Zn, Cd, Hg, Al, Ga, In, Tl, Ge, Sn, Pb, Sb and Bi.

44. A complex of claim 27, 28, 29, 30 or 31 wherein the anion $A^-$ is selected from the group consisting of $SCN^-$, $O=C=N^-$, $Cl^-$, $Br^-$, $I^-$, $F^-$, $CN^-$, $SH^-$, $S^=$, $OH^-$, $HSO_3^-$, $ClO_4^-$, $BrO_4^-$, $NH_2^-$, $NO_3^-$, $NO_2^-$, $BF_4^-$, $H^-$, $BrO^-$, $ClO^-$, $BH_4^-$, $SO_3^{--}$, $PO_4^{-3}$, $CO_3^{--}$, $SO_4^{--}$, $ClO_3^-$, $BrO_3^-$ and $AlH_4^-$.

45. A complex of claim 27, 28, 29, 30 or 31 wherein the anion $A^-$ is selected from the group consisting of the anions derived from alcohols, phenols, thiols, thiophenols, acids, amines, amides, organic compounds with mobile hydrogen, and silanols.

46. The process of claim 9 wherein the sequestering agent of formula (I) is tris(3,6,9,12tetraoxatridecyl)amine.

47. The process of claim 9 wherein the sequestering agent of formula (I) is tris(3,6,9,12,15,18hexaoxamonadecyl)amine.

48. A complex of claim 31, having the formula $[N[CH_2-CH_2-O-(CH_1-CH_2-O)_3-CH_3]_3]_y$ $[M^+A^-]$.

49. A complex of claim 31, having the formula $[N[CH_2-CH_2-O-(CH_2-CH_2-O)_5CH_3]_3]_y$ $(M^+A^-)$.

* * * * *